Figure 1:
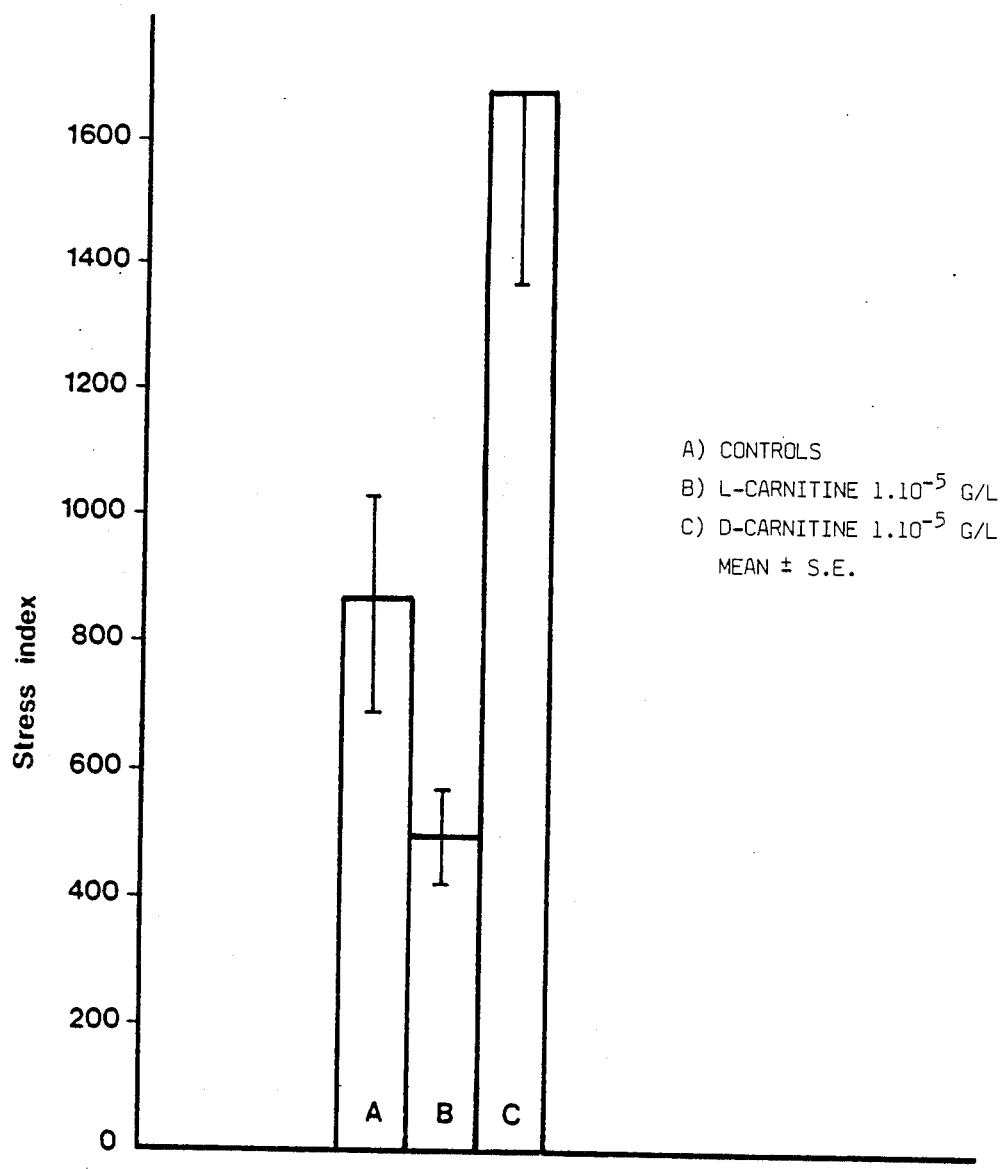

United States Patent [19]

Fanelli

[11] Patent Number: 4,656,191
[45] Date of Patent: Apr. 7, 1987

[54] PHARMACEUTICAL COMPOSITION COMPRISING L-CARNITINE FOR THE TREATMENT OF IMPAIRED CARDIAC FUNCTION

[75] Inventor: Ottorino Fanelli, Rome, Italy

[73] Assignee: Sigma-Tau Industrie Farmaceutiche Riunite S.p.A., Rome, Italy

[21] Appl. No.: 743,762

[22] Filed: Jun. 12, 1985

Related U.S. Application Data

[63] Continuation of Ser. No. 558,563, Dec. 5, 1983, abandoned, which is a continuation of Ser. No. 187,654, Sep. 16, 1980, abandoned.

[30] Foreign Application Priority Data

Sep. 21, 1979 [IT] Italy ................................ 50332 A/79

[51] Int. Cl.⁴ .......................................... A61K 31/205
[52] U.S. Cl. .................................................... 514/556
[58] Field of Search ........................................ 514/556

[56] References Cited

U.S. PATENT DOCUMENTS 4,075,352 2/1978 DeFelice ............................. 514/556
4,315,944 2/1982 Ramacci ............................. 514/556

Primary Examiner—Stanley J. Friedman
Attorney, Agent, or Firm—Ladas & Parry

[57] ABSTRACT

Further to the discovery that D-carnitine exerts an antagonistic effect versus the therapeutically advantageous effect of L-carnitine in the treatment of certain cardiac dysfunctions, a pharmaceutical composition is described for the treatment of such dysfunctions characterized by the fact that all the carnitine present therein is solely L-carnitine.

4 Claims, 4 Drawing Figures

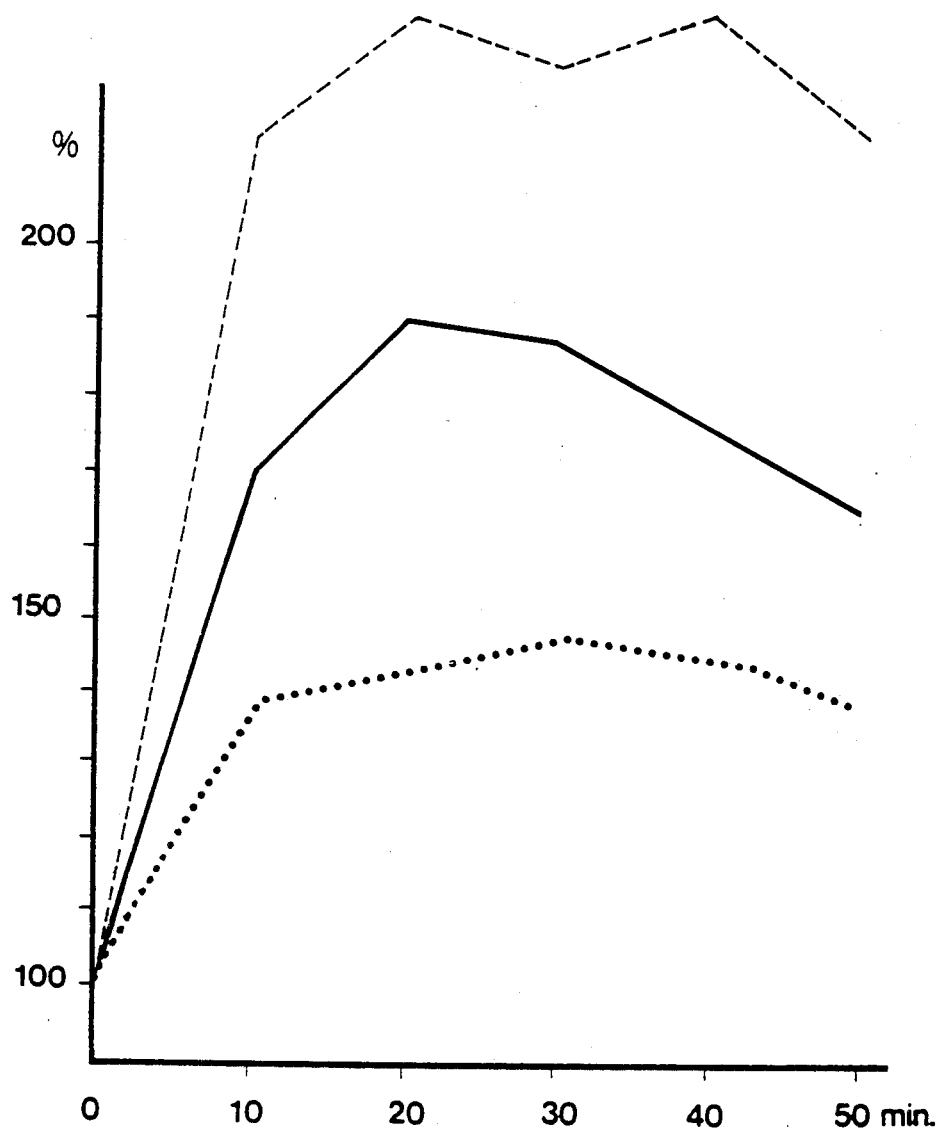
FIG. 2 EFFECT OF INFUSING D-CARNITINE (......) 5.08 mM, L-CARNITINE (_ _ _ _) 5.08 mM AND TYRODE'S SOLUTION (_____) ON CORONARY FLOW OF RAT HEART PERFUSED IN VITRO BY LANGENDORFF'S METHOD AND PRE-INFUSED WITH ADRIAMYCIN 0.20 MG/ML FOR APPROX. 60 MINUTES.

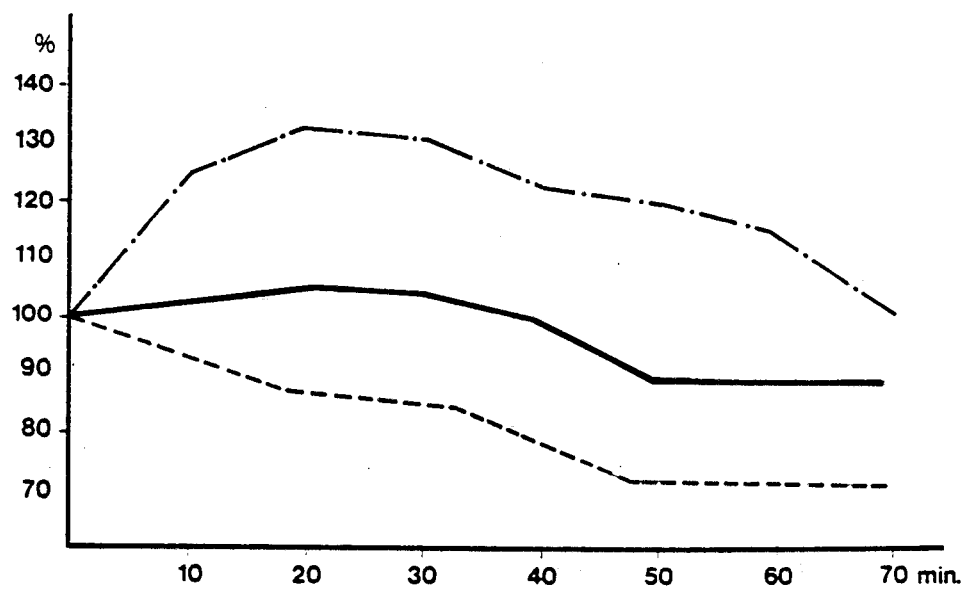

FIG. 3 EFFECT OF INFUSING D-CARNITINE (----) 5.08 mM, L-CARNITINE (-·-·-·-) 5.08 mM AND TYRODE'S SOLUTION (___) ON HEART RAT OF ISOLATED RAT HEART PERFUSED IN VITRO BY LANGENDORFF'S METHOD AND PREINFUSED WITH ADRIAMYCIN 0.20 MG/ML FOR APPROX. 60 MINUTES.

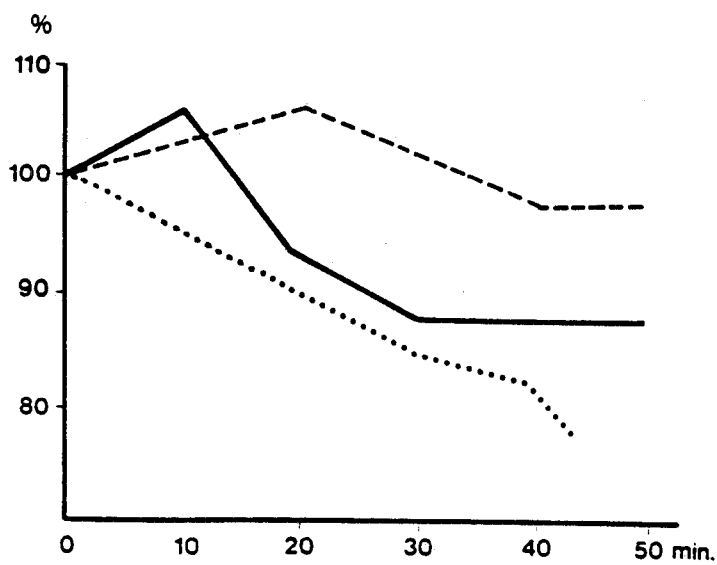

FIG. 4 EFFECT OF INFUSING D-CARNITINE (····) 5.08 mM, L-CARNITINE (------) 5.08 mM AND TYRODE'S SOLUTION (___) ON CONTRACTILE FORCE OF ISOLATED RAT HEART PERFUSED IN VITRO BY LANGENDORFF'S METHOD AND PREINFUSED WITH ADRIAMYCIN 0.20 MG/ML FOR APPROX. 60 MINUTES.

PHARMACEUTICAL COMPOSITION COMPRISING L-CARNITINE FOR THE TREATMENT OF IMPAIRED CARDIAC FUNCTION

This is a continuation of co-pending application Ser. No. 558,563, filed on Dec. 5, 1983, which is a continuation of application Ser. No. 187,654, filed on Sept. 16, 1980, both are abandoned.

The present invention concerns a pharmaceutical composition comprising L carnitine for the treatment of cardiac dysfunctions, and likewise concerns a therapeutical method comprising administering such a composition to patients affected by such dysfunctions.

The therapeutical use of carnitine ($\beta$-hydroxy-$\gamma$-trimethylamino-butyric acid) in the treatment of cardiac arrhythmias and impaired cardiac function associated with congestive heart failure and cardiogenic shock has already been disclosed in U.S. Pat. Nos. 3,830,931 and 3,968,241 issued to De Felice.

It is likewise known the $\beta$-hydroxy-$\gamma$-trimethylamino butyric acid presents an asymmetrical centre and hence occurs in the two stereoisomer forms D and L. In the aforementioned U.S. patents it is taught that ". . . either the racemate or the individual isomers can be employed. While the racemate can be conveniently employed, it appears the L isomer is more active while the D isomer is slightly more toxic". The prior art teaches therefore that, in the treatment of the aforementioned cardiac dysfunctions, the L form and the D form are both active, although a certain preference may be given to the L form versus the D form.

If it is considered that, as is well known, the resolution of a racemate into the respective optical antipodes generally involves complex and expensive processes, as in fact occurs in the case of the separation of L-carnitine from D-carnitine, and that in the aforementioned patents it is affirmed that the racemic form can be suitably employed, it is evident that the prior art as a whole in no way suggests, at least in regard to the aforementioned therapeutical purposes, the separation of the optical antipodes for the employment of L-carnitine alone, but rather to simply use carnitine in its racemic form.

It has now been surprisingly found, and is the presupposition of the present invention, that, conversely to what is taught by the known art, in the treatment of certain cardiac dysfunctions and particularly of those disclosed in the aforementioned patents to De Felice, D-carnitine is not only slightly more toxic than L-carnitine, but even exhibits a true and proper antagonistic effect against the therapeutical properties of L-carnitine. It must be well understood that it has been discovered that the D form is not simply inactive as compared to the L form, that is it does not act as a simple "diluent" of the active L form, but rather it antagonizes, at least partially inhibiting the therapeutically advantageous effect of L-carnitine.

Therefore the object of the present invention is a pharmaceutical composition for the treatment of myocardial anoxia, myocardial ischaemia, arrhythmic syndromes and heart failure, comprising an effective amount of carnitine and characterized by the fact that said carnitine is solely L-carnitine.

For the purpose of the present invention the term "solely L-carnitine" means not only that the component of the composition consisting of carnitine is substantially pure L-carnitine, that is except for eventual impurities or traces of D-carnitine, but also that carnitine, can be "prevailingly" L-carnitine, that is clearly exceeding the quantity of D-carnitine present, for instance by an L:D ratio of 95:5.

It has likewise been found that a pharamecutical composition particularly suitable for the aforementioned therapeutical uses, when in the unit dosage form, comprises from approximately 50 mg to approximately 500 mg of L-carnitine.

Therefore the scope of the present invention also includes a therapeutical method for the treatment of patients affected by myocardial anoxia, myocardial ischaemia, arrhythmic syndromes and heart failure, characterized by the fact of administering to said patients, via the oral or parenteral route, a pharmaceutical composition comprising an effective amount of carnitine present solely in the L form.

Although the daily dose to be administered depends, according to sound professional judgment, upon bodyweight, age, general conditions and the specific affection exhibited by the patient, it has been found that it is generally suitable to administer to said patients from approximately 2 mg/kg to approximately 10 mg/kg of bodyweight per day of L-carnitine.

The antagonistic effect of D-carnitine against L-carnitine has been experimentally demonstrated by means of the following techniques.

(A)

Behaviour of L- and D-carnitine on adrenaline-induced stress on isolated rabbit heat Male rabbit hearts weighing 1.6–1.8 kg were isolated as per the method described by O. Fanelli, Life Sciences, 23,2563–2570 (1978).

The hearts were perfused as per the Langendorff method (O.-Langendorff, Pfügers Arch. Ges. Physiol. 61,291–333, (1985) using a Ringer solution (which was not recycled) maintained at 38° C. and at a pressure 54 cm of water bubbled with pure oxygen.

The isometric contractions were recorded by a transducer attached via a pulley to a clip on the apex of the ventricles and regulated in such a manner as to exert a tension force of 4 grammes. By means of another transducer connected to a volume displacement recorder the coronary flow was monitored giving normal values: 22±4 ml/min.

The ECG was monitored using surface electrodes. Only hearts which initially showed a rate of at least 140 beats per minute were used. After a period of acclimatization lasting 25–30 minutes under the aforementioned experimental conditions, the basal values of the hearts to be treated with blank Ringer solution (controls) and standard Ringer solution containing L-carnitine or D-carnitine at the same concentration of $1.10^5$ g/l were recorded for 15 minutes taking care to discard hearts exhibiting some irregularities.

Cardiac stimulation was achieved by injecting 0.5 ml of Ringer solution containing 0.5 mcg of adrenaline using a lateral canula inserted into the aortic bulb. This stimulation was repeated four times at 5-minute intervals.

The stress tolerated by the heart for each injection of adrenaline was calculated by the formula:

$$[\int \Delta g \cdot i] \cdot \Delta f$$

where Δg is the increasing tension force (in grammes) and Δf is heart rate (number of beats) during the period of time (in seconds) wherein the increase in tension force occurs.

The values referring to the control hearts were compared to the respective values obtained with the hearts perfused with Ringer solution containing L-carnitine or D-carnitine, using Student's and Cochran-Cox's "t" test.

Results

Cornary flow

The basal values given in Table 1 show that L-carnitine slightly increases coronary flow, whereas D-carnitine does not.

Conversely, when adrenaline is injected D-carnitine increases the coronary-dilator effect of adrenaline, whereas L-carnitine reduces it.

Tension force peak

The data given in Table 2 show that adrenaline-induced tension force peak is decreased by L-carnitine, while D-carnitine practically does not modify it.

Duration of increased tension force induced by adrenaline

The data given in Table 3 show that the duration of increased tension force induced by adrenaline is shortened by L-carnitine, whereas D-carnitine lengthens it.

Heart rate

The data given in Table 4 show that adrenaline-induced tachycardia is reduced by L-carnitine and increased by D-carnitine.

Stress effect

The data given in Table 5 show that the stress effect is decreased by L-carnitine, whereas D-carnitine increases it.

Examination of the stress index (FIG. 1) shows that L-carnitine has an antagonizing effect on adrenaline-induced stress, while D-carnitine enhances it.

From the above experimental results it appears evident that L-carnitine reduces the three effects of stimulation on the heart exerted by adrenaline (see Tables 2,3 and 4), whereas D-carnitine even heightens the adrenaline effect on the duration of tension force and heart rate. Consequently (see Table 5 and FIG. 1) the stress index is low in the presence of L-carnitine and much higher in the presence of D-carnitine.

The antagonistic effect of the two optical isomers of carnitine is also made evident by the fact that L-carnitine reduces the coronary-dilator effect induced by adrenaline, whereas D-carnitine increases it.

(B)

Effect on adriamycin cardiotoxicity in vitro study

The action of L-carnitine and D-carnitine against adriamycin-induced cardiotoxicity was investigated using isolated rat heart perfused as per the Langendorff method, with Tyrode's solution at the rate of 0.1 ml/min.

The perfusion medium containing adriamycin at the concentration of 0.2 mg/ml was perfused on the heart until heart rate was reduced by 30% compared to the basal value. This reduced heart rate was accompanied by reduced contractile force and coronary flow rate.

Successively, Tyrode's solution containing L-carnitine or D-carnitine at a concentration of 5.08 mM or Tyrode's blank solution (control group) was perfused on the heart for 90–120 min.

The graphs appearing in FIGS. 2, 3 and 4 show that the repairing effect against cardiac damage caused by adriamycin administration is exclusively exerted by L-carnitine, whereas D-carnitine exhibits an opposite effect antagonizing that of L-carnitine. D-carnitine appears incapable of even partially restoring cardiac function.

(C)

Effect on experimental infarctions (control infarction and test infarction) induced in the same heart by occlusion of two coronary arteries in the dog.

The technique described by W. Shaper, M. Hofmann, K. D. Müller, K. Genth and M. Carl in Basic Res. Cardiol., 74, 224–229 (1979) was employed, with simultaneous occlusion of two coronary arteries in the same heart, for producing ischaemic areas with equal dimensions in identical haemodynamic conditions.

Successively, one of the ischaemic areas was perfused with a D-carnitine solution and the other with L-carnitine. Both solutions had the same concentration of carnitine (approx. 0.5 millimoles).

It was determined that, while the extension of the ischaemic area perfused with the D-carnitine solution remained unchanged, the extension of the ischaemic area perfused with the L-carnitine solution was reduced by approximately 60% as compared to the pre-infusion value.

TABLE 1

Isolated rabbit heart. Four adrenaline injections (0.5 mcg) with 5-minute intervals between injections. Changes in coronary flow ml/min.(mean ± S.E.)

| Groups | no. of hearts | basal values | adrenaline 0.5 mcg % values | | | |
|---|---|---|---|---|---|---|
| | | | $1^{st}$ injection | $2^{nd}$ injection | $3^{rd}$ injection | $4^{th}$ injection |
| Controls | 9 | 23.6 ± 1.50 | −0.76 ± 6.65 | −5.86 ± 5.45 | +7.85 ± 8.24 | +12.74 ± 5.06 (a) |
| L-carnitine $1 \cdot 10^{-5}$ g/l | 9 | 27.0 ± 0.91 | −14.6 ± 6.43 | +5.97 ± 5.38 | +3.73 ± 6.08 | +0.21 ± 4.05 |
| D-carnitine $1 \cdot 10^{-5}$ g/l | 11 | 23.4 ± 1.02 | −3.09 ± 3.01 | +6.63 ± 6.16 | +10.6 ± 3.48 (b) | +9.83 ± 2.62 (c) |

Statistically significant values versus controls (a) $0.05 > p > 0.02$, (b) $0.02 > p > 0.01$, (c) $0.01 > p > 0.001$

TABLE 2

As in Table 1.
Tension force increase peak (grammes) (mean ± S.E.)

| Groups | no. of hearts | $1^{st}$ injection | adrenaline 0.5 mcg | | |
|---|---|---|---|---|---|
| | | | $2^{nd}$ injection | $3^{rd}$ injection | $4^{th}$ injection |
| Controls | 9 | 2.82 ± 0.41 | 2.92 ± 0.32 | 3.17 ± 0.35 | 3.43 ± 0.59 |
| L-carnitine $1 \cdot 10^{-5}$ g/l | 9 | 1.73 ± 0.23 (a) | 2.23 ± 0.08 | 2.68 ± 0.23 | 3.02 ± 0.33 |
| D-carnitine $1 \cdot 10^{-5}$ g/l | 11 | 2.48 ± 0.30 | 3.12 ± 0.27 | 3.13 ± 0.30 | 3.22 ± 0.29 |

Statistically significant differences versus controls (a) $0.05 > p > 0.02$.

TABLE 3

As in Table 1. Tension force duration (seconds) induced by adrenaline (mean ± S.E.)

| Groups | no. of hearts | 1st injection | adrenaline 0.5 mcg | | |
|---|---|---|---|---|---|
| | | | 2nd injection | 3rd injection | 4th injection |
| Controls | 9 | 49.2 ± 5.15 | 61.4 ± 9.81 | 61.0 ± 6.63 | 71.0 ± 10.1 |
| L-carnitine $1 \cdot 10^{-5}$ g/l | 9 | 37.8 ± 3.66 | 50.4 ± 4.48 | 55.7 ± 5.93 | 58.6 ± 5.31 |
| D-carnitine $1 \cdot 10^{-5}$ g/l | 11 | 73.5 ± 8.70 (a) | 80.0 ± 11.2 | 83.5 ± 9.05 | 86.2 ± 11.4 |

Statistically significant differences versus controls (a) $0.05 > p > 0.02$.

TABLE 4

As in Table 1. Increase in heart rate, beats/minute (mean ± S.E.)

| Groups | no. of hearts | basal values | adrenaline 0.5 mcg | | | |
|---|---|---|---|---|---|---|
| | | | 1st injection | 2nd injection | 3rd injection | 4th injection |
| Controls | 9 | 184 ± 6.5 | +22 ± 13.5 | +29 ± 3.5 | +29 ± 6.8 | +26 ± 11.8 |
| L-carnitine $1 \cdot 10^{-5}$ g/l | 9 | 178 ± 4.6 | +33 ± 6.7 | +32 ± 10.0 | +44 ± 10.0 | +33 ± 13.4 |
| D-carnitine $1 \cdot 10^{-5}$ g/l | 11 | 177 ± 4.4 | +53 ± 4.1 (*) | +46 ± 6.1 | +53 ± 9.8 | +46 ± 4.7 |

(*)Statistically significant differences versus controls $0.05 > p > 0.02$.

TABLE 5

As in table 1. Effect of stress $[\int \Delta g.t] \cdot \Delta r/100$ (mean ± S.E.)

| Groups | no. of hearts | 1st injection | adrenaline 0,5 mcg | | |
|---|---|---|---|---|---|
| | | | 2nd injection | 3rd injection | 4th injection |
| Controls | 9 | 105.8 ± 16.5 | 182 ± 40.8 | 203.5 ± 41.5 | 294.6 ± 89.1 |
| L-carnitine $1 \cdot 10^{-5}$ g/l | 9 | 48.0 ± 9.4 (c) | 94.4 ± 14.6 | 153.0 ± 31.2 | 183.3 ± 43.5 |
| D-carnitine $1 \cdot 10^{-5}$ g/l | 11 | 255.4 ± 44.2 (b) | 432.4 ± 95.6 | 425.2 ± 85.4 | 492.0 ± 123.3 |

Two composition examples for the manufacture of tablets are given hereunder

| Example 1 | |
|---|---|
| L-carnitine | 330.0 mg |
| Magnesium stearate | 50.0 mg |
| Microcrystalline cellulose | 240.0 mg |
| | 620.0 mg |

| Example 2 | |
|---|---|
| L-carnitine | 330.0 mg |
| Stearic acid | 35.0 mg |
| Microcrystalline cellulose | 230.0 mg |
| | 595.0 mg |

What is claimed is:

1. A therapeutical method for the treatment of patients affected by arrhythmic syndromes and congestive heart failure, characterized by the fact of administering to said patients, via the oral or parenteral route, a pharmaceutical composition comprising an effective amount of L-carnitine substantially free of D-carnitine.

2. The therapeutical method according to claim 1 characterized by the fact of administering to said patients approximately 2 mg to approximately 10 mg/kg of bodyweight per day of said composition.

3. The method of claim 2 wherein said L-carnitine is administered in tablets comprising 330.0 mg L-carnitine, 50 mg magnesium stearate, and 240.0 mg microcrystalline cellulose.

4. The method of claim 2 wherein said L-carnitine is administered in tablets comprising 330 mg L-carnitine, 350 mg stearic acid, and 230.0 mg microcrystaline cellulose.